United States Patent [19]

Foote et al.

[11] Patent Number: 5,047,015

[45] Date of Patent: Sep. 10, 1991

[54] LOCKING SYRINGE

[75] Inventors: Jerrold L. Foote; Darla R. Gill; Fred P. Lampropoulos, all of Salt Lake City; William Padilla, Bennion, all of Utah

[73] Assignee: Merit Medical Systems, Inc., Salt Lake City, Utah

[21] Appl. No.: 434,460

[22] Filed: Nov. 13, 1989

Related U.S. Application Data

[63] Continuation-in-part of Ser. No. 325,561, Mar. 17, 1989.

[51] Int. Cl.⁵ ............................................ A61M 29/00
[52] U.S. Cl. ...................................... 604/99; 604/96; 604/98; 604/224; 606/194
[58] Field of Search ................. 128/675; 604/96–100, 604/103, 109, 118, 220, 224, 225, 227, 207–208; 606/191, 192, 194

[56] References Cited

U.S. PATENT DOCUMENTS

| 383,940 | 6/1888 | Brinkerhoff . |
| 404,105 | 5/1889 | Overlach . |
| 466,125 | 2/1891 | Schirmer . |
| 577,682 | 2/1897 | Eissner . |
| 730,054 | 6/1903 | Sheets . |
| 1,661,818 | 3/1928 | Cook . |

(List continued on next page.)

FOREIGN PATENT DOCUMENTS

| 545415 | 8/1957 | Canada . |
| 1242737 | 8/1960 | France . |
| 2083364A | 3/1982 | United Kingdom . |

OTHER PUBLICATIONS

"ACS Accessories Offer Optimum Efficiency in Your Angioplasty Procedures", Eli Lilly and Company.
"Clearing the Path for a Healthy Heart", *Tristate: The Cincinnati Enquirer Magazine*, Oct. 23, 1988.
"Coronary Angioplasty", Krames Communications, 1985.
"Good News for People with Only Tow Hands", SciMed Life Systems, Inc.
"Heath—Critis of Angioplasty Worry About Inflated Success Claims", *U.S. News & World Report*, Jul. 25, 1988, p. 65.
"Inflation PRO: A New Dual-Support System for Angioplasty", Baxter Healthcare Corporation.
"PTCA Safe and Efficacious Performed Together with Diagnostic Angiography in Selected Cases", *Cardiovascular News*, May 1988, p. 8.
"USCI Wizard Disposable Inflation Device", C.R. Bard, Inc.

*Primary Examiner*—Stephen C. Pellegrino
*Assistant Examiner*—Michael Rafa
*Attorney, Agent, or Firm*—Workman Nydegger Jensen

[57] ABSTRACT

A syringe and method for use which may be selectively operated between a freely reciprocating position and a restricted position. A triggering means configured with a trigger attached to the plunger of the syringe is employed. The triggering means includes threads located external of the plunger and corresponding threads internal of the barrel of the syringe. Upon actuation of the trigger, the threads on the plunger are retracted from their position of engagement with the threads on the barrel, thereby placing the syringe in position for free sliding movement of the plunger with respect to the barrel. The trigger is biased to the engaged position so that if the trigger is released, the threads on the plunger return to their position of engagement with the threads on the barrel. In the restricted position, the plunger may be screwed into or out of the barrel by rotating the plunger, enabling the operator of the syringe to maintain strict control over the amount of pressure in the syringe. The triggering means employs a plurality of ramp and channel configurations which are disposed at approximately the same angel as the threads on the plunger and barrel which direct the retraction of the threads on the plunger from engagement to disengagement with the threads on the barrel.

85 Claims, 4 Drawing Sheets

U.S. PATENT DOCUMENTS

| | | |
|---|---|---|
| 1,707,880 | 4/1929 | Sheets . |
| 2,656,836 | 10/1953 | Hickey ................................ 128/218 |
| 2,672,866 | 3/1954 | Kater ................................. 128/218 |
| 2,699,168 | 1/1955 | Lewis ................................ 128/218 |
| 2,724,385 | 11/1955 | Lockhart ............................ 128/261 |
| 2,736,315 | 2/1956 | Feeney .............................. 128/218 |
| 2,764,978 | 10/1956 | Everett .............................. 128/215 |
| 3,080,866 | 3/1963 | Friedman ........................... 128/218 |
| 3,388,941 | 6/1968 | Marcus .................................. 294/1 |
| 3,478,937 | 11/1969 | Solowey ............................. 222/386 |
| 3,491,757 | 1/1970 | Arce .................................. 128/221 |
| 3,884,229 | 5/1975 | Raines et al. ................... 128/218 N |
| 4,057,050 | 11/1977 | Sarstedt ................................ 127/2 |
| 4,063,662 | 12/1977 | Drummond ............................ 222/31 |
| 4,254,773 | 3/1981 | Waldbilling ....................... 128/348 |
| 4,267,846 | 5/1981 | Kontos ............................... 128/765 |
| 4,439,185 | 3/1984 | Lundquist ............................ 604/99 |
| 4,444,335 | 4/1984 | Wood ................................... 222/43 |
| 4,466,426 | 8/1984 | Blackman ............................ 128/1.1 |
| 4,504,268 | 3/1985 | Herlitze .............................. 604/170 |
| 4,568,335 | 2/1986 | Updike et al. ..................... 604/224 |
| 4,573,978 | 3/1986 | Reilly ................................. 604/240 |
| 4,583,974 | 4/1986 | Kokernak ............................. 604/99 |
| 4,601,701 | 7/1986 | Mueller, Jr. ......................... 604/83 |
| 4,710,179 | 12/1987 | Haber et al. ....................... 604/211 |
| 4,715,854 | 12/1987 | Vaillancourt ....................... 604/191 |
| 4,723,938 | 2/1988 | Goodin et al. ....................... 604/97 |
| 4,743,230 | 5/1988 | Nordquest ............................ 604/97 |
| 4,758,223 | 7/1988 | Rydell ................................. 604/98 |
| 4,787,429 | 11/1988 | Valentini et al. ................... 141/383 |
| 4,819,637 | 4/1989 | Dormandy, Jr. et al. .......... 128/325 |
| 4,825,876 | 5/1989 | Beard ................................. 128/675 |
| 4,832,692 | 5/1989 | Box et al. ............................ 604/99 |
| 4,838,864 | 6/1989 | Peterson ............................. 604/118 |
| 4,919,121 | 4/1990 | Rydell et al. ......................... 604/97 |
| 4,940,459 | 7/1990 | Noce .................................... 604/98 |

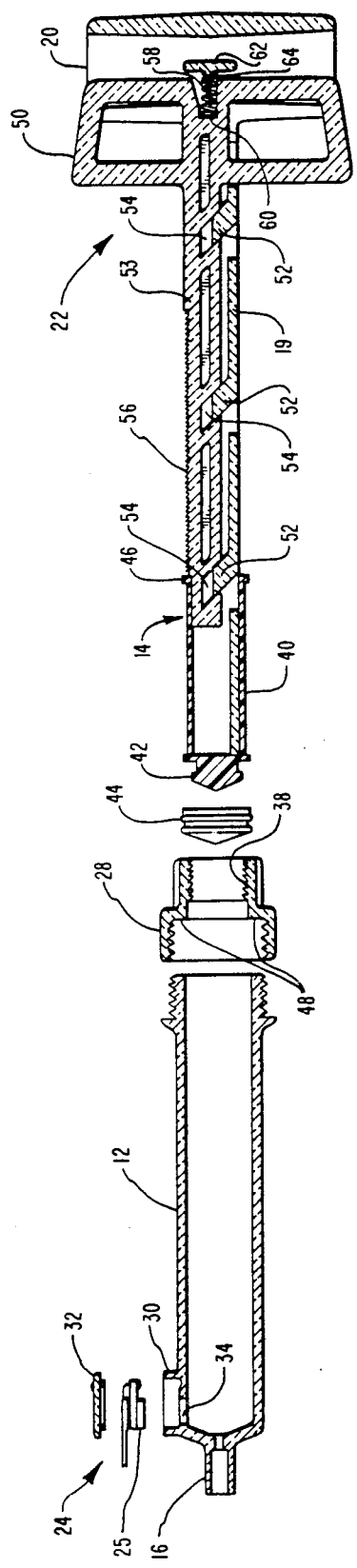

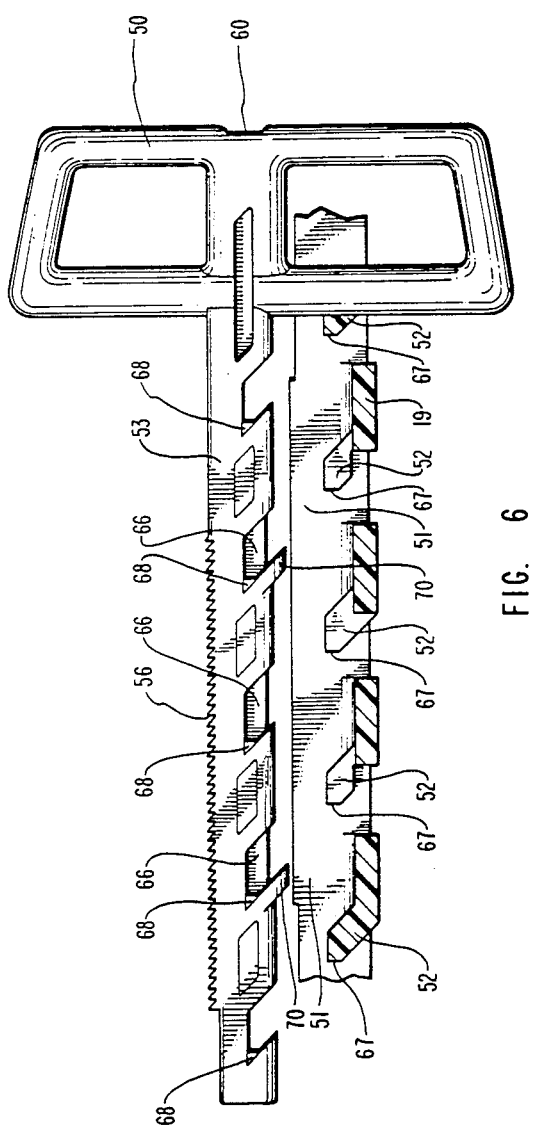
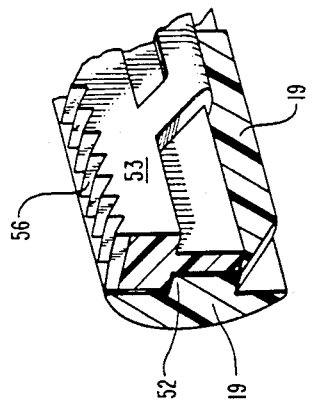
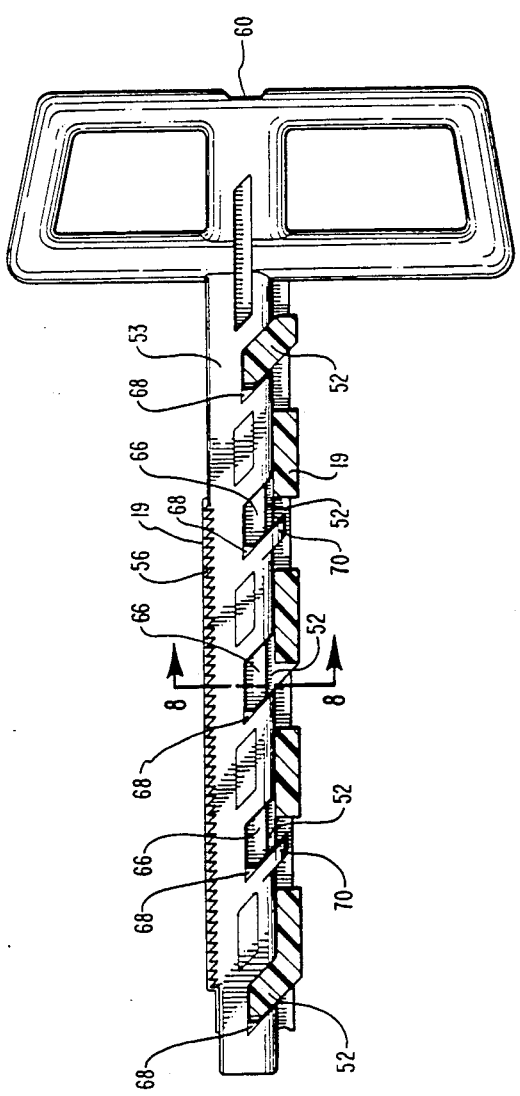
FIG. 6
FIG. 8
FIG. 7

LOCKING SYRINGE

RELATED APPLICATIONS

This application is a continuation-in-part of U.S. patent application Ser. No. 07/325,561, filed Mar. 17, 1989, entitled "Locking Syringe" and naming Jerrold L. Foote, Darla R. Gill, Fred R. Lampropoulos and William Padilla as inventors.

FIELD OF THE INVENTION

The present invention relates to methods and apparatus for a syringe which operates selectively between a freely reciprocating mode and a threaded mode. More particularly, the present invention relates to a locking syringe and methods of use which incorporate a triggering device on the plunger of the syringe which may be actuated to retract threads located on the plunger of the syringe to enable the plunger to move with respect to the barrel in both a freely reciprocating mode and a locked, or threaded, mode.

BACKGROUND OF THE INVENTION

One of the most basic of the tools used by the medical practitioner is the syringe. Perhaps best known as an instrument used with a needle to inject medicine into a patient, the syringe has also been found useful in a variety of other applications. For example, syringes are particularly useful in performing angiographic procedures.

Angioplasty is a procedure for reducing the blockage which may occur in blood vessels. Over time, blood vessels may become partially or totally blocked due to buildup of cholesterol plaque along the walls of the vessel.

One location where plaque buildup is particularly dangerous is within the coronary arteries. The coronary arteries are those arteries which supply oxygen-rich blood to the heart. Buildup of plaque within the coronary arteries, a condition commonly referred to as coronary artery disease, can cause serious chest pain—angina—and, if not treated, may eventually cause heart failure.

Coronary angioplasty involves opening these blocked coronary arteries by inserting a balloon-tipped catheter into the artery. The balloon is inserted by making an incision usually in the groin or arm. A catheter is then inserted in a blood vessel exposed by the incision and threaded into the coronary artery.

An x-ray sensitive dye is injected into the coronary artery to enable the clinician to accurately position the catheter in the blocked portion of the artery. The catheter is inserted along the artery until the section of the catheter on which the balloon is located is positioned along the blocked portion of the artery.

A fluid is injected into the catheter to inflate the balloon. As the balloon is inflated, the plaque is compressed thereby expanding the narrowed artery. The clinician then withdraws the fluid from the balloon catheter, causing the balloon to deflate. The balloon catheter may then be removed from the patient.

It has been found that a syringe provides an effective tool for the introduction of fluid into the balloon catheter. However, because the pressure within the balloon must be carefully controlled during the angioplasty procedure, typical syringes having a plunger which may be freely depressed into the barrel are inadequate for this application.

If the pressure within the balloon is too great, the balloon may burst, a circumstance which usually requires immediate emergency surgery to correct. Some prior art attempts at designing a syringe which provides greater control over the pressures achieved in the balloon include providing a syringe which incorporates a plunger which is threadably connected to the barrel. Thus, the plunger may be slowly threaded into the barrel, resulting in a more controlled introduction of fluid into the balloon catheter.

A serious disadvantage to such syringes is the inability to freely and rapidly move the plunger in and out of the barrel in sliding reciprocation. For example, a preferred method of deflating the balloon is to rapidly withdraw the plunger from the barrel to create a negative pressure thereby causing the fluid to exit the balloon in an attempt to equilibrate the pressure within the balloon catheter. Withdrawing the plunger gradually from the barrel of the syringe by "unscrewing" the plunger requires a great amount of time and, more significantly, results in reduced effectiveness in deflating the balloon.

In recognition of the desirability of a syringe having a plunger/barrel assembly capable of operating in both a free or freely reciprocating mode and a threaded or restricted mode, syringes have been developed which address this problem. Most such syringes employ a thread engagement mechanism on the barrel of the syringe which can be actuated to selectively engage and disengage the threads on the plunger.

When the thread engagement mechanism is engaged, the syringe is "locked" into a threaded mode so that free reciprocating movement of the plunger sliding within the barrel is prevented. In this locked position, the plunger may only be moved within the barrel by rotation—gradually screwing it into or out of the barrel.

A serious design flaw which exists in some syringes employing a thread engagement mechanism on the barrel of the syringe is that the syringe is awkward to use. When using the syringe, one must grasp the barrel with one hand an, depress the plunger with the other hand, taking care to steadily hold the syringe as the plunger is depressed. Depending on the location and direction of actuation of the thread engagement mechanism, it can be difficult to properly hold the syringe in a steady position and control the thread engagement mechanism at the same time.

An additional disadvantage to such syringes is that some prior art syringes require that the barrel of the syringe be aligned in a certain orientation before the thread engagement mechanism can be actuated. This makes the syringe more difficult to use because the user must first ensure that the syringe is properly aligned before actuating the thread engagement mechanism.

A potentially serious flaw exists in some syringe designs which incorporate a thread engagement mechanism which, when actuated, causes slight movement of the plunger. This movement of the plunger could cause an unwanted and potentially dangerous increase or decrease in the pressure within the balloon.

If the balloon were to be expanded beyond acceptable limits, the coronary artery being repaired might be expanded beyond its capacity to yield. Rupture of the coronary artery would require immediate emergency surgery to correct, and, depending on the severity of the rupture, might require immediate bypass surgery.

Many prior art syringes also suffer from the disadvantage that it is impossible to view the fluid within the syringe along its entire path into the balloon catheter. During angioplasty, it is important to prevent air bubbles from entering the balloon catheter. If an air bubble were to enter the balloon and the balloon were to burst, the resulting embolism could cause serious injury to the patient's heart and possibly result in the patient's death.

Apart from angioplasty, other medical applications also benefit from a "locking" syringe. For example, such a syringe could be advantageously employed in a biopsy procedure—removing a tissue or cell sample from a patient to be later tested and further examined in a laboratory.

Such a syringe could be utilized in this way to avoid having to subject the patient to more serious surgical procedures to obtain the sample. A needle could be attached to the syringe and inserted into the patient such that the end of the needle contacts the tissue desired to be sampled.

The plunger could then be rapidly withdrawn from the barrel of the syringe to create a negative pressure within the barrel of the syringe. The effect of the negative pressure would be to draw sample tissue into the needle. Utilizing a locking syringe enables the clinician to lock the plunger in this retracted position to preserve the negative pressure and free the clinician from having to hold the plunger in the desired position.

However, many of the problems and disadvantages discussed above with respect to angioplasty syringes also exist in syringes used for biopsy.

It will be appreciated, therefore, that what is needed in the art are methods and apparatus which may be used to inject a fluid under pressure and enable the operator of the syringe to maintain a significant degree of control over the pressures obtained.

It would be an advancement in the art to provide an apparatus and method for a syringe in which the plunger is capable of selectively operating freely with respect to the barrel and operating in a "locked" or threaded mode.

It would also be an advancement in the art to provide an apparatus and method for such a syringe which is not awkward to operate because of positioning of a thread engagement mechanism located on the barrel of the syringe.

It would be a further advancement in the art if such an apparatus and method could be employed with a syringe such that the syringe may be actuated between freely reciprocating mode and a threaded or restricted mode of operation irrespective of the orientation of the barrel of the syringe.

It would be yet a further advancement in the art to provide methods and apparatus for a syringe which would enable the syringe to be actuated between a free position and a threaded position without any movement of the plunger with respect to the barrel during such actuation.

It would be an additional advancement in the art if such a syringe and methods could be provided that would permit the user of the syringe to observe the existence of air bubbles within the syringe and along the path of the fluid being injected by the syringe.

The foregoing, and other features and objects of the present invention, are realized in the locking syringe disclosed and claimed herein.

BRIEF SUMMARY AND OBJECTS OF THE INVENTION

The present invention is directed to a locking syringe and its methods of use. The syringe includes a novel plunger and barrel combination which allows the syringe to be selectively operated between a freely reciprocating mode—wherein the plunger may slide freely within the barrel in a reciprocating manner—and a locked, or threaded, mode—wherein the reciprocating movement of the plunger is restricted by placing the plunger in threaded engagement with the barrel. In the locked or engaged position, the plunger may be screwed into or out of the barrel by rotating the plunger, thereby resulting in controlled and gradual reciprocating movement of the plunger relative to the barrel. Additionally, if no force is applied to the plunger to cause it to rotate, the plunger remains locked against any movement of the plunger with respect to the barrel. Thus, one operating the syringe in the locked or restricted mode can maintain precise control over the amount of pressure exerted by the syringe.

The syringe incorporates a triggering device which is actuated by a trigger located on the plunger. This convenient positioning of the trigger enables the clinician to easily operate the trigger to actuate the triggering device using the same hand with which the plunger is actuated to operate the syringe, regardless of whether the locking syringe is maintained in the free position or in the locked position.

In a preferred embodiment of the invention, the triggering device is incorporated into the neck of the plunger and includes threads and a series of channels disposed along a spine. Ramps corresponding to each channel are located along an elongated groove in the neck of the plunger such that the spine rests in the groove and each ramp is at least partially disposed within its corresponding channel. Upon actuation of the triggering device, the channels travel along the ramps, causing the spine and thereby the threaded portion of the triggering device to be retracted from engagement with corresponding threads on the barrel. In this retracted position, the plunger may freely reciprocate slidably within the barrel.

Advantageously, the ramps and channels are disposed at an acute angle with respect to the vertical which is less than or equal to the angle of disposition with respect to the vertical of the primary teeth on the threads. Thus, as the triggering device is actuated and the channels slide along the ramps, the threads on the triggering device are retracted from the threads on the barrel without any net force resulting which would cause movement of the plunger with respect to the barrel.

When the syringe is designed for angioplasty, it may also be provided with an integral transducer means for measuring the amount of pressure exerted on fluid being injected by the syringe, as more particularly described in copending U.S. patent Application Ser. No. 324,938, which is incorporated herein by specific reference.

The barrel and tip of the syringe are preferrably made of a transparent material. Thus, the operator of the syringe may visually verify whether air bubbles are located within the liquid being injected with the syringe.

It is, therefore, a primary object of the present invention to provide a syringe which provides the operator of the syringe with the capability of selectively operating the syringe in a freely reciprocating mode or to maintain precise control over the amount of pressure exerted by the syringe by operating the syringe in a threadably restricted mode.

An additional object of the present invention is to provide a syringe and methods for use thereof by which selective operation in both a freely reciprocating mode and a locked or threaded mode, can be accomplished using the same hand used to actuate the plunger.

It is also an object of the present invention to provide such a syringe which incorporates a triggering mechanism having a trigger disposed on the plunger of the syringe, thereby facilitating the use of the syringe.

It is a further object of the present invention to provide a syringe which may be selectively operated between the locked and free positions regardless of the orientation of the barrel of the syringe.

Still another object of the present invention is to provide such a locking syringe which incorporates a triggering device which may be actuated to convert the syringe from a restricted threaded mode to a freely reciprocating mode, and vice versa, without resulting in any significant reciprocating movement of the plunger with respect to the barrel.

Another important object of the present invention is to provide such a syringe which is made of a transparent material such that the entire path of the fluid being injected by the syringe may be viewed by the operator of the syringe to ensure that the liquid does not contain any air bubbles.

Other objects and advantages of the present invention will become more fully apparent upon reading the following detailed description and appended claims, and upon reference to the accompanying drawings, or by the practice of the invention.

BRIEF DESCRIPTION OF THE DRAWINGS

FIG. 2 is an exploded, longitudinal-section view of the syringe illustrated in FIG. 1.

FIG. 3 is a longitudinal-section view of the syringe according to the present invention illustrating the locked or restricted position.

FIG. 3A is an enlarged view of a portion of the internal and external threads illustrated in FIG. 3.

FIG. 4 is a longitudinal-section view illustrating the syringe of FIG. 3 with the triggering device actuated and the syringe in the freely reciprocating position.

FIG. 6 is a sectional view of a portion of the plunger illustrating another preferred embodiment of the triggering device and the neck of the plunger.

FIG. 7 is a sectional view of a portion of the plunger illustrated in FIG. 6 showing the spine of the triggering device in a fully retracted position.

FIG. 8 is a cut-away cross-sectional view along line 8—8 of FIG. 7 shown in perspective which illustrates the intermeshing of channels and ramps of the triggering device.

DETAILED DESCRIPTION OF THE PREFERRED EMBODIMENTS

Figure 1:
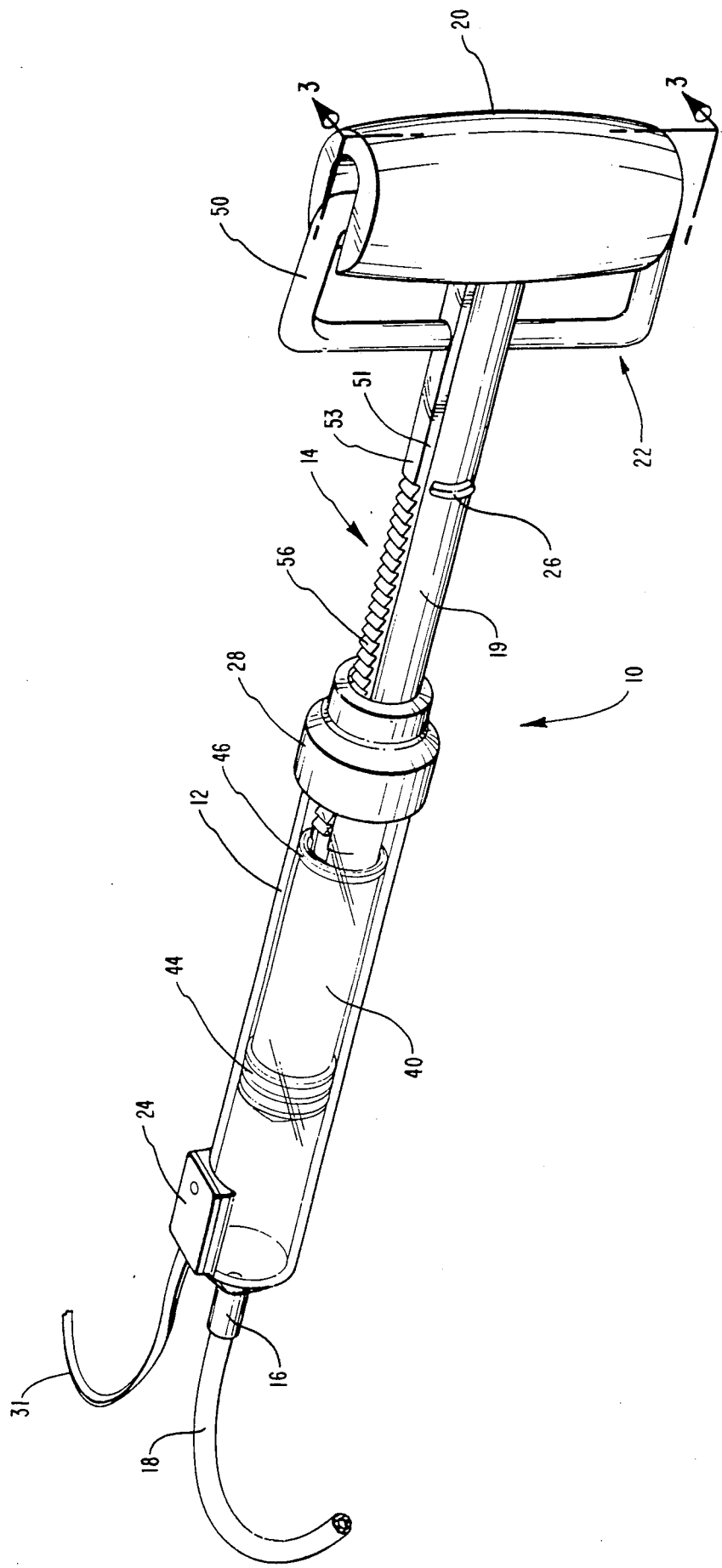
FIG. 1 is a perspective view of a presently preferred embodiment of the locking syringe of the present invention.

Reference is now made to the drawings wherein like parts are designated with like numerals throughout. Referring now to FIG. 1, one presently preferred embodiment of the present invention is illustrated and designated generally at 10.

The syringe 10 includes a barrel 12 and a plunger 14. The barrel 12 has a plunger insertion end and a lead end and is equipped at the lead end with a tip 16. A piece of tubing 18 may be attached to the tip 16. The tubing 18 may be connected to a rotatable connector, such as a luer connector, and attached to a balloon catheter (not shown) thereby creating a conduit for fluid communication between the barrel 12 and the balloon catheter for use in angioplasty. Alternatively, a needle may be attached to the syringe at tip 16, thereby enabling the syringe to be used for a biopsy application or an application requiring controlled injection. It will be appreciated that there are a variety of applications for the locking syringe of the present invention and, according to the application, an appropriate attachment may be attached to the syringe at tip 16.

With continued reference to FIG. 1, the plunger 14 further comprises a neck 19 and a handle 20 at one end of the neck 19. The plunger 14 is also configured with a means for triggering the selection of the mode of operation of the syringe whether it be the freely reciprocating mode or the treadedly restricted mode. The means for triggering such selection utilizes a triggering device 22. As will be explained in greater detail below, the triggering device 22 may be actuated to selectively place the plunger 14 in threaded engagement with the barrel 12 or to enable the plunger 14 to freely reciprocate slidably within the barrel 12.

With reference now to FIG. 2, the barrel 12 further includes a cap 28 which is threadably connected to the end of the barrel 12 opposite tip 16. Cap 28 is provided to facilitate assembly of the syringe 10. Cap 28 also includes internal restricting means such as internal helical threads 38 which, as will be explained in greater detail below, may engage corresponding threads on the plunger 14.

The plunger 14 is configured with a collar 40 having a bulb adaptor 42 at one end. The function and configuration of collar 40 is set forth in greater detail in copending U.S. patent Application Ser. No. 07/173,447, filed Mar. 25, 1988, entitled DISPOSABLE CONTROL SYRINGE. A rubber bulb 44, such as those known in the art, is attached to the bulb adaptor 42.

In operation, the collar 40 of the plunger remains disposed within the barrel 12. Means are provided on the plunger 14 to retain the collar 40 within the barrel 12. It is presently preferred that a disc 46 be configured on the end of collar 40 for this purpose. As the plunger 14 is slidably extracted from the barrel 12, the disc 46 will engage and abut against lip 48 of the cap 36 to prevent further extraction of the plunger 14.

The barrel 12 of the syringe further includes transducer means 24 in fluid communication with the interior of barrel 12 for measuring the fluid pressure within the barrel 12. In the presently preferred embodiment, the transducer means 24 is located at the end of barrel 12, near tip 16, as illustrated in FIGS. 1–3.

In order to effectively measure the pressure within the barrel 12, the transducer means 24 is ideally always in fluid contact, directly or indirectly, with the fluid in the interior of the barrel 12. To prevent the plunger 14 from being inserted into the barrel 12 and blocking the fluid contact between the transducer means 24 and the barrel 12, a stop 26 is configured on the plunger 14 (See FIG. 1).

The stop 26 acts to prevent the plunger 14 from being inserted into the barrel 12 beyond the location of the stop 26. It will be appreciated that a variety of other means may be employed for preventing the plunger from blocking fluid contact between transducer means 24 and the fluid in the interior of the barrel 12. For example, a ridge could be provided along the interior of the barrel 12 adjacent the transducer means 24 which would accomplish the same result.

With reference now specifically to FIG. 2, the transducer means 24 comprises, for example, a piezoresistive semiconductor integrated circuit chip 25 which mounts within a housing 30 integrally configured on the end of barrel 12. The transducer chip 25 and electrical cable 31 attached thereto are secured in housing 30 with a suitable potting compound, and a transducer cover 32 is provided to enclose the entire assembly in housing 30. A small opening 34 permits the fluid contact between the transducer chip 25 and the fluid in the interior of the barrel 12. As discussed above, stop 26 serves as a means to prevent the plunger 14 from being inserted into the barrel 12 to the point where bulb 44 would cover opening 34.

Still referring to FIG. 2, the triggering device 22 includes a trigger 50 in connection with the plunger 14. In a presently preferred embodiment, the trigger 50 is disposed proximate to the handle 20 to facilitate actuating the trigger 50 with the same hand used to grasp the handle 20. It will be appreciated that the trigger 50 may also be disposed at various locations along the plunger 14.

The triggering device 22 of plunger 14 further includes an extended longitudinal groove 51 having a series of ramps 52 disposed along the walls of the groove 51 and a spine 53 having a corresponding channel 54 for each ramp 52. The spine 53 is disposed within groove 51 such that each ramp 52 is disposed in register with and at least partially within the corresponding channel 54 during the operation of the syringe 10, whether the mode of operation is the freely reciprocating mode or the threadedly restricted mode. Although in a presently preferred embodiment of the invention three or four sets of ramps and channels are employed, it will be appreciated that the number of ramps and channels is largely a matter of design choice. It has been found that increasing the number of ramps and channels may lend stability to the plunger and prevent unwanted deflection in the triggering device 22. Further, although the preferred embodiment has the channels disposed on the spine 53 and the ramps 52 disposed on the walls of the groove 51, it should be understood that the channels 54 could be disposed along the walls of the groove 51 of neck 19 and the ramps 52 could be disposed along the spine 53.

In a preferred embodiment of the triggering device 22, external threads 56 are configured along one side of the spine 53 of the triggering device 22. The external threads 56 are configured such that they may threadably engage internal threads 38 located within cap 28. FIG. 1 illustrates that the external threads 56 are non-continuous; that is, the tooth pattern does not continue around the spine 53 to connect adjacent teeth to one another.

The triggering device 22 is further configured with means for biasing the external threads 56 into threaded engagement with internal threads 38 and means for biasing the trigger 50 in a nonactuated position. One presently preferred mechanism for accomplishing this function is to employ a spring 58, as illustrated in FIG. 2, which rests between a notch 60 in trigger 50 and against a post 62 attached to handle 20.

The post 62 includes a nib 64 which fits inside the end of the spring 58 resting against post 62. The nib 64 assists in positioning spring 58 against post 62 and preventing the spring 58 from sliding along post 62. Thus, post 62 and nib 64 act to properly position the trigger 50 with respect to the handle 20 and to assist in preventing any lateral movement of the trigger 50 with respect to the handle 20.

The operation of the locking syringe may be best explained with reference to FIGS. 3, 3A, and 4. In FIG. 3, a locking syringe 10 according to the present invention is illustrated in the locked, or threaded, position. In the "locked" position, the plunger 14 is in threaded engagement with the barrel 12 by the engagement of external threads 56 and internal threads 38. Due to such threaded engagement the slidably reciprocating movement of the plunger 14 within barrel 12 is restricted. A force applied to the handle 20 of the syringe along the longitudinal direction (substantially in the direction of arrow A) will not result in movement of the plunger 14 with respect to the barrel 12. Thus, the force of back pressure on the fluid being dispensed by the syringe will not cause the plunger 14 to recede under the pressure, nor will an inadvertent over compression of the plunger 14 occur.

In the locked or restricted position, the plunger 14 may, however, be moved in and out of the barrel 12 by rotating the handle 20. Depending on the pitch of the threads 56 and 38, the plunger 14 will move in a helical path which translates to a predetermined longitudinal distance within the barrel 12 with each rotation of the handle 20. In this manner, the rotational movement of the plunger 14 causes gradual longitudinal movement of the rubber bulb 44 within the barrel 12 thus effectuating slight pressure differences in the material being injected or extracted by the syringe 10. In some applications, such as angioplasty, when the syringe 10 is used to exert a controlled pressure, the ability to obtain slight longitudinal movements of the plunger or to move the plunger to a predetermined point of insertion are necessary for obtaining and exactly controlling the desired pressures.

FIG. 4 illustrates the syringe 10 of the present invention with the triggering device 22 actuated to place the syringe 10 in the freely reciprocating mode of operation. With the triggering device 22 so actuated, a longitudinally directed force applied to the handle 20 of the syringe will result in the substantially unrestricted slidable movement of the plunger 14 longitudinally within the barrel 12. Thus, rapid movement of the plunger 14 with respect to the barrel 12 may be obtained with the syringe 10 in the free position.

Many applications requiring a locking syringe also require that the syringe be capable of operating in such a free position. For example, when performing angioplasty, it is first necessary to fill the balloon catheter with a liquid before applying pressure on the liquid to expand the balloon within the blocked blood vessel. Initially, filling the balloon catheter can be quickly and easily accomplished with the syringe in the free position.

Also, when the angioplasty procedure is completed and it is desired to deflate the balloon, the balloon may be most efficiently deflated by creating a negative pressure within the syringe 10 which will act to extract the liquid out of the balloon catheter, thereby deflating the balloon. The creation of negative pressure within the syringe 10 can be effectively accomplished with the syringe 10 in the free position.

Still referring to FIG. 4, the triggering device 22 is actuated by applying a force on the trigger 5) in the direction of arrow B. Unlike prior art type syringes, this may be advantageously done by the clinician with a one-handed squeezing movement and using the same hand that moves the syringe plunger 14. The clinician grasps handle 20 and by squeezing the trigger 50 and handle 20 is able to, apply a force on the trigger 50 in the direction of arrow B and an equal and opposite force on the handle 20. Thus, there is no resulting net force on the plunger 14 which would tend to move the plunger 14 in or out of the barrel 12. The force applied to the trigger 50 acts to compress spring 58 and causes the channels 54 to slide over the ramps 52.

Figure 5:
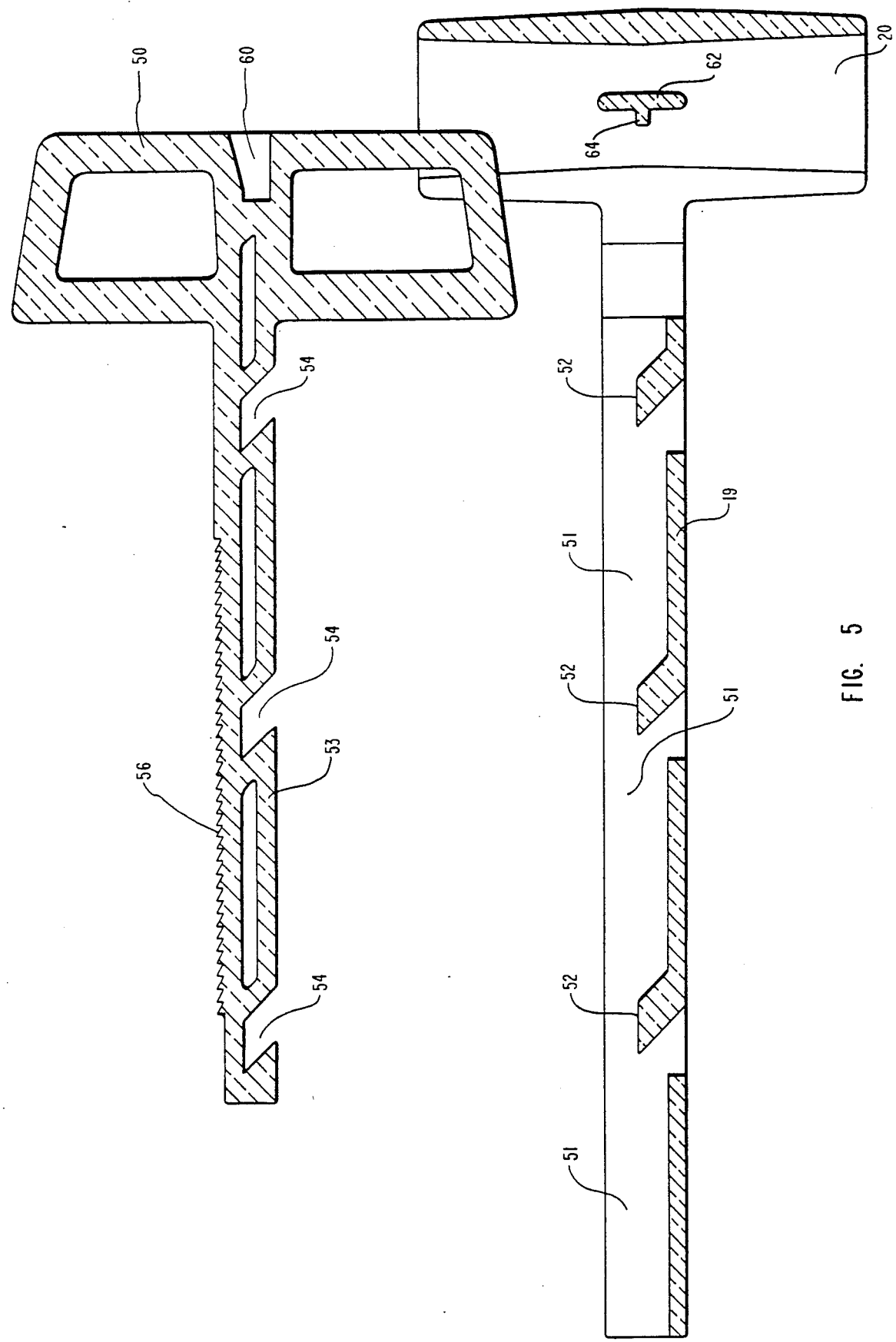
FIG. 5 is a longitudinal-section view illustrating the separate pieces which comprise a preferred embodiment of a portion of the plunger showing the handle and triggering device according to the present invention.

Two primary components which comprise the triggering device 22 are separately illustrated in FIG. 5. As illustrated in FIG. 5, neck 19 is connected to the handle 20, and spine 53 is connected to trigger 50 which lies within the groove 51 configured along the longitudinal length of the neck 19. When assembled, as illustrated in FIGS. 3 and 4, the channels 54 each engage a ramp 52.

As the triggering device 22 is actuated by applying a force to trigger 50 in the direction of arrow B, the spine 53 retracts in the direction in which the channels 54 are forced to travel along the ramps 52. As the channels 54 travel along the ramps 52, the external threads 56 located on the spine 53 are retracted from engagement with the internal threads 38.

The direction of retraction of the external threads 56 is dictated by the angle of the ramps 52. For example, a presently preferred angle of disposition of the ramps 52 is approximately 45 degrees with respect to the transverse plane of the plunger 14, as viewed in FIG. 4. Thus, as the external threads 56 are retracted upon actuation of the triggering device 22, the threads move both longitudinally in the direction of arrow B and laterally in the direction of arrow C.

In some applications for which a locking syringe, such as a syringe according to the present invention, is utilized, it is preferred that the triggering device 22 may be actuated to change the syringe from the locked mode to the free mode, or vice versa, without any perceptible resulting movement of the plunger 14 with respect to the barrel 12. Movement of the plunger 14 with respect to the barrel 12 may be avoided as the external threads 56 are retracted from engagement with the internal threads 38, if the angle of the external and internal threads is greater than or equal to the angle of disposition of the ramps 52 and channels 54 so that the direction of retraction is at an angle that will not cause the threads to bind against each other.

FIG. 3A is an enlarged view of the internal and external threads 38 and 56 of FIG. 3 and illustrates the non-symmetry of the teeth. As can be observed in FIG. 3A, each tooth of the external threads 56 has a leading edge 72 and a trailing edge 74. Also, the teeth on internal threads 38 have a leading edge 76 and a trailing edge 78. The leading edges 72 of external threads 56 and the leading edges 76 of internal threads 38 are preferably disposed at angles with respect to each other which permit the teeth to mesh properly. The same is true of trailing edge 74 of external threads 56 and trailing edge 78 of internal threads 38.

In a preferred embodiment, trailing edges 74 and 78 are disposed at substantially the same acute angle with respect to the vertical as the acute angle of disposition with respect to the vertical of ramps 52 and channels 54. Thus, as the external threads 56 are moved from a position of engagement to a position of disengagement, teeth on exterior threads 56 retract without contacting the trailing edge 78 of the teeth on the internal threads 38 which would cause movement of the plunger 14 into the barrel 12. Conversely, as the external threads 56 are moved from a position of disengagement to a position of engagement, minimal movement, if any, is imparted to the plunger 14 within the barrel 12. Significant movement would result in a significant increase in the pressure being exerted by the syringe 10 which, as noted above, is not acceptable for certain appications of a locking syringe.

If slight increases of pressure within the barrel 12 of the syringe 10 as the triggering device 22 is actuated can be tolerated for certain applications, a variety of combinations of angles may be utilized. It has been found that an approximate 45 degree ramp angle is preferable.

The leading edges 72 and 76 of the threads preferably are disposed at an angle of approximately two degrees from the vertical (the direction of arrow C). This two degree draft is primarily to assist in removing the parts from their molds during the manufacturing process when the parts are molded from plastic.

In order to prevent the plunger 14 from ratcheting back when a substantial back pressure is built up inside the barrel 12 of the syringe 10 (pressures of up to approximately 20 atmospheres are not uncommon for angioplasty applications), the ramps 52 are canted towards the tip 16 of the barrel 12. However, for other applications, it may be desirable to reverse the orientation of the ramps 52. For example, when the locking syringe 10 is used primarily or exclusively for creating substantial negative pressures, the ramps 52 may be canted away from the tip 16, to prevent the plunger 14 from ratcheting into the barrel 12 as substantial negative pressures are developed.

When it is desired to release the syringe 10 from the freely reciprocating position and have it return to the locked or restricted position, the force being applied to trigger 50 is released. Acting under the biasing force of spring 58, the spine 53 will travel up the ramps 52 and return the external threads 56 to their position of threaded engagement with the internal threads 38, as illustrated in FIG. 3.

With the trigger 50 attached to the plunger 4 of the syringe 10, the triggering device 22 may be actuated regardless of the rotational orientation of handle 20 to the barrel 12. To actuate the triggering device 22, the operator of the syringe 10 need only grasp the barrel 12 with one hand and hold the handle 20 with the other hand. The trigger 50 may then be easily actuated with the hand which is holding the handle 20.

In another preferred embodiment of the present invention, shown in FIGS. 6–8, the strength and stability of the plunger 14 is enhanced by reducing the amount of empty space within the mechanism of the triggering device 22 and the wear on the external threads 56 is reduced by increasing the amount of retraction so that the spine 53 retracts fully into the groove 51. Spine 53 has channels 54 which are arranged in pairs in which each channel 54 of a pair is in lateral register with the other channel 54 and they are separated by support gussets 66 disposed longitudinally and centered along the spine 53. The support gussets 66 add rigidity and strength to the spine 53 over the embodiment illustrated in FIGS. 3 and 4. Consequently, ramps 52 are provided on each side of groove 51 that register with the channels 54. To reduce the likelihood that ramps 52 may snag preventing full retraction of the spine 53 into groove 51, the ramps 52 have a bevelled leading edge 67. Each channel 54 of the spine 53 has a wedge 68 which compliments the bevelled leading edge 67 of each ramp 52 when the spine 53 is fully retracted. The wedges 68 add volume and further stability to the spine 53. Also, at least one protruding arm 70 is provided to assist maintaining the orientation of the spine 53 within the groove 51 and in guiding the retraction of the spine 53 along the ramps 52 and to enhance the lateral stability of the plunger 14.

FIG. 7 shows the spine 53 fully retracted into groove 51 so that the top edge of the external threads 56 do not extend beyond the upper edge of neck 19. In this manner, during free sliding reciprocation of the plunger 14 within barrel 12 there will be no grinding or undesired racheting of the external threads 56 and the internal threads 38. Such grinding and racheting causes wear to the teeth and possibly breakage.

As can be seen in FIG. 8, the preferred embodiment illustrated significantly reduces the amount of empty space within the mechanism of the triggering device 22, thereby increasing the strength and stability of the plunger 14.

It will be appreciated by one skilled in the relevant art that a syringe according to the present invention may be made of a variety of materials. However, it is presently preferred that the barrel 12, including the tip 16, be made of a transparent material, such as a clear plastic. Thus, the operator of the syringe can visually ascertain whether there are any air bubbles in the contents of the barrel 12.

It will be appreciated that the apparatus and methods of the present invention are capable of being incorporated in the form of a variety of embodiments, only a few of which have been illustrated and described above. The invention may be embodied in other forms without departing from its spirit or essential characteristics. The described embodiments are to be considered in all respects only as illustrative and not restrictive, and the scope of the invention is, therefore, indicated by the appended claims rather than by the foregoing description. All changes which come within the meaning and range of equivalency of the claims are to be embraced within their scope.

What is claimed and desired to be secured U.S. Letters patent is:

1. A locking syringe for holding a syringe plunger in a selected position against a pressure created within a syringe barrel by sliding movement of the plunger to the selected position within the barrel, the syringe comprising:
    a barrel having internal restricting means;
    a plunger for disposition at least partially within said barrel, said barrel receiving said plunger in reciprocating, sliding engagement, said plunger comprising:
        external restricting means situated along at least a portion of the longitudinal axis of said plunger and corresponding to said internal restricting means such that said external restricting means is capable of engaging said internal restricting means thereby restricting the reciprocating, sliding engagement of said plunger within said barrel;
    a triggering means for actuating engagement and disengagement of said external restricting means with said internal restricting means by selective retraction of said external restricting means situated along said portion of the longitudinal axis of said plunger, whereby the sliding engagement of said plunger within said barrel is restricted if said external restricting means and said internal restricting means maintain a position of engagement, and said plunger is free to reciprocate slidably within said barrel if said external restricting means is retracted so as to maintain a position of disengagement relative to said internal restricting means; and
    means for increasing the force with which said external restricting means engages said internal restricting means in proportion to the pressure within said barrel exerted on said plunger.

2. A locking syringe as set forth in claim 1, wherein said external restricting means is retractable from engagement with said internal restricting means and said triggering means actuates retraction of said external restricting means from engagement with said internal restricting means into the position of disengagement.

3. A locking syringe as set forth in claim 2, wherein said triggering means comprises a trigger connected to said external restricting means, said trigger being capable of movement from a first position to a second position, said first position corresponding to the position of engagement; said second position corresponding to the position of disengagement such that if said trigger is moved from said first position to said second position such movement actuates the retraction of said external restricting means from engagement with said internal restricting means into the position of disengagement.

4. A locking syringe as set forth in claim 3, wherein said trigger is urged into said first position by a means for exerting a predetermined biasing force thereby requiring the application of a force, greater than the biasing force, to move said trigger from said first position to said second position and to maintain said trigger in said second position, and if such force is removed from said trigger, said trigger will return to said first position under the biasing force.

5. A locking syringe as set forth in claim 1, wherein said triggering means situated relative to said plunger so as to be is capable of being actuated without regard to the rotational orientation of said plunger relative to said barrel.

6. A locking syringe as set forth in claim 1, wherein said internal restricting means comprise internal threads disposed within said barrel and said external restricting means comprise external threads disposed on said plunger which may meet in threaded engagement.

7. A locking syringe as set forth in claim 6, wherein said external threads are noncontinuous.

8. A locking syringe as set forth in claim 2, wherein said internal restricting means comprises internal threads disposed within said barrel and said external restricting means comprises external threads disposed on said plunger which are capable of meeting in threaded engagement and the retraction of said external restricting means from said internal restricting means is at an angle which is less than or equal to the angle defined by the teeth of the internal threads, whereby the retraction may be actuated without appreciable movement of said plunger within said barrel.

9. A locking syringe as set forth in claim 3, wherein said triggering means further comprises at least one ramp and at least one channel wherein each said ramp is in register and in sliding engagement with at least one of said channels; said ramp sliding within said channel as said trigger is moved from said first position to said second position.

10. A locking syringe as set forth in claim 9, wherein said triggering means further comprises at least one support gusset disposed between a pair of said channels.

11. A locking syringe as set forth in claim 9, wherein said ramps and said channels cant at an acute angle to the transverse plane of said plunger, such acute angle defining the angle of the retraction of said external restricting means from said internal restricting means.

12. A locking syringe as set forth in claim 9, wherein adjacent at least one of said channels is a protruding arm in sliding engagement with one of said ramps; said protruding arm for guiding the sliding engagement of said ramp within said channel.

13. A locking syringe as set forth in claim 1, wherein said external restricting means is disposed along a spine which is connected to said triggering means and said plunger further comprises a neck portion having an elongate groove; said spine is disposed within said groove in sliding engagement.

14. A locking syringe as set forth in claim 13, wherein said triggering means comprises a trigger connected to said spine, said trigger being capable of movement from a first position to a second position, said first position corresponding to the position of engagement; said second position corresponding to the position of disengagement such that if said trigger is moved from said first position to said second position such movement actuates the retraction of said external restricting means from engagement with said internal restricting means into the position of disengagement.

15. A locking syringe as set forth in claim 14, wherein if said trigger is fully actuated said spine is fully retracted into said groove of said neck portion of said plunger such that no portion of said external restricting means protrudes beyond the outside edge of said groove.

16. A locking syringe as set forth in claim 15, wherein at least one channel is disposed on said spine and at least one ramp is disposed on said neck portion of said plunger, wherein each said ramp is in register and in sliding engagement with at least one of said channels; said ramp sliding within said channel as said trigger is moved from said first position to said second position.

17. A locking syringe as set forth in claim 16, wherein a plurality of channels is disposed on said spine and said channels are situated in pairs in lateral register, each pair being separated by a support gusset.

18. A locking syringe as set forth in claim 16, wherein at least one of said ramps comprises a bevelled edge to facilitate the sliding engagement of said ramp within its corresponding channel.

19. A locking syringe as set forth in claim 18, wherein said spine comprises at least one wedge adjacent one of said channels; said wedge engaging said bevelled edge of said ramp in substantially flush abutment.

20. A locking syringe as set forth in claim 1, further comprising a stop means for restricting said plunger from movement into said barrel beyond a predetermined point of insertion.

21. A locking syringe as set forth in claim 20, wherein said stop means is disposed on the external surface of said plunger.

22. A locking syringe as set forth in claim 1, further comprising a cap; said cap being removably connected to said barrel.

23. A locking syringe as set forth in claim 22, wherein said plunger further comprising a collar wherein said cap abuts said collar thereby preventing said plunger from being fully extracted from said barrel if said plunger is withdrawn to its fullest extent.

24. A locking syringe as set forth in claim 1, wherein said plunger is restricted to rotational movement within said barrel if said external restricting means is in engagement with said internal restricting means.

25. A locking syringe as set forth in claim 24, wherein said triggering means is situated relative to said plunger so that the triggering means may be actuated without regard to the rotational orientation of said plunger within said barrel.

26. A locking syringe as set forth in claim 1, wherein said plunger is restricted to helical rotational movement if said external restricting means is in engagement with said internal restricting means, whereby the insertion and extraction of said plunger is continuously controlled by the rotation of said plunger.

27. A locking syringe as set forth in claim 1, wherein said barrel further comprises a cap and said internal restricting means is disposed within said cap.

28. A locking syringe as set forth in claim 27, wherein said cap is removable from said barrel.

29. A locking syringe as set forth in claim 1, wherein said barrel is transparent.

30. A locking syringe, comprising:
a barrel comprising a cap having internal restricting means disposed within said cap;
a plunger for disposition at least partially within said barrel, said barrel receiving said plunger in reciprocating, sliding engagement, said plunger comprising:
spring-biased external restricting means situated along at least a portion of the longitudinal axis of said plunger and corresponding to said internal restricting means such that said external restricting means is normally engaging said internal restricting means thereby restricting the reciprocating, sliding engagement of said plunger within said barrel; and
a triggering means for actuating disengagement of said spring-biased external restricting means with said internal restricting means by selective retraction of said external restricting means situated along said portion of the longitudinal axis of said plunger, whereby the sliding engagement of said plunger within said barrel is restricted if said external restricting means is retracted so as to maintain a position of disengagement relative to said internal restricting means.

31. A locking syringe as set forth in claim 30, wherein said barrel has a plunger insertion end and a lead end and said pressure sensing means is disposed proximate to the lead end.

32. A locking syringe as set forth in claim 30, wherein said external restricting means is retractable from engagement with said internal restricting means and said triggering means actuates the retraction of said external restricting means from engagement with said internal restricting means into the position of disengagement.

33. A locking syringe as set forth in claim 32, wherein said triggering means comprises a trigger connected to said external restricting means, said trigger being capable of movement from a first position to a second position, said first position corresponding to the position of engagement; said second position corresponding to the position of disengagement such that if said trigger is moved from said first position to said second position such movement actuates the retraction of said external restricting means from engagement with said internal restricting means into the position of disengagement.

34. A locking syringe as set forth in claim 33, wherein said trigger is urged into said first position by a means for exerting a predetermined biasing force thereby requiring the application of a force, greater than the biasing force, to move said trigger from said first position to said second position and to maintain said trigger in said second position, and if such force is removed from said trigger, said trigger will return to said first position under the biasing force.

35. A locking syringe as set forth in claim 30, wherein said triggering means is situated relative to said plunger so as to be capable of being actuated without regard to the rotational orientation of said plunger relative to said barrel.

36. A locking syringe as set forth in claim 30, wherein said internal restricting means comprise internal threads disposed within said barrel and said external restricting means comprise external threads dispose on said plunger which may meet in threaded engagement.

37. A locking syringe as set forth in claim 36, wherein said external threads are noncontinuous.

38. A locking syringe as set forth in claim 32, wherein said internal restricting means comprises internal threads disposed within said barrel and said external restricting means comprises external threads disposed on said plunger which are capable of meeting in threaded engagement and the retraction of said external restricting means rom said internal restricting means is at an angle which is less than or equal to the angle defined by the teeth of the internal threads, whereby the retraction may be actuated without appreciable movement of said plunger within said barrel.

39. A locking syringe as set forth in claim 33, wherein said triggering means further comprises at least one ramp and at least one channel wherein each said ramp is in register and in sliding engagement with at least one of said channels; said ramp sliding within said channel as said trigger is moved from said first position to said second position.

40. A locking syringe as set forth in claim 39, wherein said triggering means further comprises at least ore support gusset disposed between a pair of said channels.

41. A locking syringe as set forth in claim 39, wherein said ramps and said channels cant at an acute angle to the transverse plane of said plunger, such acute angle defining the angle of the retraction of said external restricting means from said internal restricting means.

42. A locking syringe as set forth in claim 39, wherein adjacent at least one of said channels is a protruding arm in sliding engagement with one of said ramps; said protruding arm for guiding the sliding engagement of said ramp within said channel.

43. A locking syringe as set forth in claim 30, wherein said external restricting means is disposed along a spine which is connected to said triggering means and said plunger further comprises a neck portion having an elongate groove; said spine is disposed within said groove in sliding engagement.

44. A locking syringe as set forth in claim 43, wherein said external restricting means is retractable from engagement with said internal restricting means and said triggering means actuates retraction of said external restricting means from engagement with said internal restricting means into the position of disengagement.

45. A locking syringe as set forth in claim 44, wherein said triggering means comprises a trigger connected to said spine, said trigger being capable of movement from a first position to a second position, said first position corresponding to the position of engagement; said second position corresponding to the position of disengagement such that if said trigger is moved from said first position to said second position such movement actuates the retraction of said external restricting means from engagement with said internal restricting means into the position of disengagement.

46. A locking syringe as set forth in claim 45, wherein if said trigger is fully actuated said spine is fully retracted into said groove of said neck portion of said plunger such that no portion of said external restricting means protrudes beyond the outside edge of said groove.

47. A locking syringe as set forth in claim 46, wherein at least one channel is disposed on said spine and at least one ramp is disposed on said neck portion of said plunger, wherein each said ramp is in register and in sliding engagement with at least one of said channels; said ramp sliding within said channel as said trigger is moved from said first position to said second position.

48. A locking syringe as set forth in claim 47, wherein a plurality of channels is disposed on said spine and said channels are situated in pairs in lateral register, each pair being separated by a support gusset.

49. A locking syringe as set forth in claim 47, wherein at least one of said ramps comprises a bevelled edge to facilitate the sliding engagement of said ramp within its corresponding channel.

50. A locking syringe as set forth in claim 49, wherein said spine comprises at least one wedge adjacent one of said channels; said wedge engaging said bevelled edge of said ramp in substantially flush abutment.

51. A locking syringe as set forth in claim 30, further comprising a stop means for restricting said plunger from movement into said barrel beyond a predetermined point of insertion.

52. A locking syringe as set forth in claim 51, wherein said stop is disposed on the external surface of said plunger.

53. A locking syringe as set forth in claim 30, further comprising a cap; said cap being removably connected to said barrel.

54. A locking syringe as set forth in claim 53, wherein said plunger further comprising a collar wherein said cap abuts said collar thereby preventing said plunger from being fully extracted from said barrel if said plunger is withdrawn to its fullest extent.

55. A locking syringe as set forth in claim 30, wherein said plunger is restricted to rotational movement within said barrel if said external restricting means is in engagement with said internal restricting means.

56. A locking syringe as set forth in claim 55, wherein said triggering means is situated relative to said plunger so that the triggering means may be actuated without regard to the rotational orientation of said plunger within said barrel.

57. A locking syringe as set forth in claim 30, wherein said plunger is restricted to helical rotational movement if said external restricting means is in engagement with said internal restricting means, whereby the insertion and extraction of said plunger is continuously controlled by the rotation of said plunger.

58. A locking syringe as set forth in claim 30, wherein said cap is removable from said barrel.

59. A locking syringe as set forth in claim 30, wherein said barrel is transparent.

60. An angioplasty syringe for inflating and deflating a balloon catheter and for holding a plunger in a selected position against a pressure created within a barrel by sliding the plunger to the selected position within the barrel, comprising:
   a barrel having internal restricting means, said barrel also having a plunger insertion end and a lead end wherein the balloon catheter is connectable to the lead end of said barrel via a tube such that the balloon catheter is in fluid communication with the contents of said barrel;
   a pressure sensing means for sensing the pressure of the contents within said barrel;
   a plunger for disposition at least partially within said barrel, said barrel receiving said plunger in reciprocating, sliding engagement, said plunger comprising:
   external restricting means situated along at least a portion of the longitudinal axis of said plunger and corresponding to said internal restricting means such that said external restricting means is capable of engaging said internal restricting means thereby restricting the reciprocating, sliding engagement of said plunger within said barrel;
   a triggering means for actuating engagement and disengagement of said external restricting means with said internal restricting means by selective retraction of said external restricting means situated along said portion of the longitudinal axis of said plunger, whereby the sliding engagement of said plunger within said barrel is restricted if said external restricting means and said internal restricting means maintain a position of engagement, and said plunger is free to reciprocate slidably within said barrel if said external restricting means is retracted so as to maintain a position of disengagement relative to said internal restricting means; and
   means for increasing the force with which said external restricting means engages said internal restricting means in proportion to the pressure within said barrel exerted on said plunger.

61. An angioplasty syringe as set forth in claim 60, wherein said triggering means comprises a trigger connected to said external restricting means, said trigger being capable of movement from a first position to a second position, said first position corresponding to the position of engagement; said second position corresponding to the position of disengagement such that if said trigger is moved from said first position to said second position such movement actuates the retraction of said external restricting means from engagement with said internal restricting means into the position of disengagement.

62. An angioplasty syringe as set forth in claim 61, wherein said trigger is urged into said first position by a means for exerting a predetermined biasing force thereby requiring the application of a force, greater than the biasing force, to move said trigger from said first position to said second position and to maintain said trigger in said second position, and if such force is removed from said trigger, said trigger will return to said first position under the biasing force.

63. An angioplasty syringe as set forth in claim 60, wherein said external restricting means is disposed along a spine which is connected to said triggering means and said plunger further comprises a neck portion having an elongate groove; said spine is disposed within said groove in sliding engagement.

64. An angioplasty syringe as set forth in claim 63, wherein said external restricting means is retractable from engagement with said internal restricting means and said triggering means actuates retraction of said external restricting means from engagement with said internal restricting means into the position of disengagement.

65. An angioplasty syringe as set forth in claim 64, wherein said triggering means comprises a trigger connected to said spine, said trigger being capable of movement from a first position to a second position, said first position corresponding to the position of engagement; said second position corresponding to the position of disengagement such that if said trigger is moved from said first position to said second position such movement actuates the retraction of said external restricting means from engagement with said internal restricting means into the position of disengagement.

66. An angioplasty syringe as set forth in claim 65, wherein if said trigger is fully actuated said spine is fully retracted into said groove of said neck portion of said plunger such that no portion of said external restricting means protrudes beyond the outside edge of said groove.

67. An angioplasty syringe as set forth in claim 66, wherein at least one channel is disposed on said spine and at least one ramp is disposed on said neck portion of said plunger, wherein each said ramp is in register and in sliding engagement with at least one of said channels; said ramp sliding within said channel as said trigger is moved from said first position to said second position.

68. An angioplasty syringe as set forth in claim 67, wherein a plurality of channels is disposed on said spine and said channels are situated in pairs in lateral register, each pair being separated by a support gusset.

69. An angioplasty syringe as set forth in claim 60, further comprising a stop, said stop to restrict said plunger from movement into said barrel beyond a predetermined point of insertion thereby preventing the blockage of said pressure sensing means from pressure communication with the contents of said barrel by said plunger.

70. An angioplasty syringe as set forth in claim 60, wherein said plunger is restricted to helical rotational movement if said external restricting means is in engagement with said internal restricting means, whereby the insertion and extraction of said plunger is controlled by the rotation of said plunger enabling the controlled slight increase and decrease of pressure within said barrel and thereby controlling the inflation and deflation of the balloon of the balloon catheter.

71. An angioplasty syringe as set forth in claim 70, wherein said triggering means is situated relative to said plunger so as to be capable of being actuated without regard to the rotational orientation of said plunger within said barrel, thereby permitting the extraction of said plunger to rapidly deflate the balloon.

72. An angioplasty syringe as set forth in claim 60, wherein said barrel is transparent.

73. A method for selectively operating a syringe between a freely reciprocating mode and a restricted mode, the syringe comprising a barrel and a plunger wherein the plunger is disposed at least partially within the barrel and is selectively locked against a pressure created in the barrel, comprising the steps of:
   placing the syringe into the restricted mode by directing external restricting means disposed on at least a portion of the longitudinal axis of the plunger into engagement with internal restricting means within the barrel so that reciprocating movement of the plunger within the barrel is restricted;
   increasing the force with which such external restricting means engages said internal restricting means in proportion to the pressure within said barrel exerted on said plunger;
   actuating a triggering means by applying a force to the triggering means whereby the triggering means moves in response to the force and the external restricting means is retracted and thereby disengages the internal restricting means such that the plunger is free to slidably reciprocate within the barrel; and
   releasing the application of force to the triggering means whereby the triggering means moves in response to the removal of the force and the external restricting means engages the internal restricting means such that the plunger is restricted from freely slidable reciprocation within the barrel.

74. A method as set forth in claim 73, wherein the triggering means is biased into a position of engagement and the application of force requires a force greater than the biasing force to actuate the triggering means whereby the external restricting means may be moved to a position of disengagement.

75. A method as set forth in claim 73, wherein the plunger is rotatable if the syringe is in the restricted mode of operation and comprising the additional step of rotating the plunger.

76. A method as set forth in claim 75, wherein the plunger travels a helical path if rotated thereby changing the extent of insertion of the plunger within the barrel and comprising the additional step of adjusting the extent of insertion of the plunger within the barrel.

77. A method as set forth in claim 76, further comprising the steps of activating a pressure sensing means for sensing the pressure of the contents within the barrel for monitoring the pressure of the contents within the barrel and rotating the plunger until a desired pressure is obtained.

78. A method as set forth in claim 75, wherein said triggering means is capable of being actuated without regard to the rotational orientation of the plunger to the barrel and comprising the additional step of actuating the triggering means by applying a force to the triggering means whereby the triggering means moves in response to the force and the external restricting means disengages the internal restricting means such that the plunger is free to slidably reciprocate within the barrel.

79. A method for selectively operating an angioplasty syringe between a freely reciprocating mode and a restricted mode, the syringe comprising a barrel connected in fluid communication with a balloon catheter and with a pressure sensing means and a plunger wherein the plunger is disposed at least partially within the barrel and is selectively locked against a pressure created in the barrel, comprising the steps of:
   placing the syringe into the restricted mode by directing external restricting means disposed on at least a portion of the longitudinal axis of the plunger into engagement with internal restricting means within the barrel so that reciprocating movement of the plunger within the barrel is restricted to rotational movement;
   increasing the force with which such external restricting means engages said internal restricting means in proportion to the pressure within said barrel exerted on said plunger;
   actuating a triggering means by applying a force to the triggering means whereby the triggering means moves in response to the force and the external restricting means is retracted and thereby disengages the internal restricting means such that the plunger is free to slidably reciprocate within the barrel; and
   releasing the application of force to the triggering means whereby the triggering means moves in response to the removal of the force and the external restricting means engages the internal restricting means such that the plunger is restricted from freely slidable reciprocation within the barrel.

80. A method as set forth in claim 79, wherein the triggering means is biased into a position of engagement and the application of force requires a force greater than the biasing force to actuate the triggering means whereby the external restricting means may be moved to a position of disengagement.

81. A method as set forth in claim 79, wherein the plunger travels a helical path if rotated thereby changing the extent of insertion of the plunger within the barrel and comprising the additional step of adjusting the extent of insertion of the plunger within the barrel thereby adjusting the inflation of the balloon of the balloon catheter.

82. A method as set forth in claim 81, comprising the additional steps of activating the pressure sensing means for monitoring the pressure of the contents within the barrel and rotating the plunger until the desired inflation of the balloon of the balloon catheter is obtained.

83. A method as set forth in claim 81, wherein said triggering means is capable of being actuated without regard to the rotational orientation of the plunger to the barrel and comprising the additional step of actuating the triggering means by applying a force to the triggering means whereby the triggering means moves in response to the force and the external restricting means disengages the internal restricting means such that the plunger is free to slidably reciprocate within the barrel.

84. A method as set forth in claim 83, comprising the additional step of extracting the plunger rapidly to rapidly deflate the balloon of the balloon catheter.

85. A method for selectively operating syringe for the extraction of tissue for analysis between freely reciprocating mode and a restricted mode, the syringe comprising a barrel connected to a tissue collecting needle and a plunger, the plunger is disposed at least partially within the barrel, comprising the steps of:
   positioning the plunger fully inserted within the barrel;
   placing the syringe into the restricted mode by directing external restricting means disposed on the plunger into engagement with internal restricting means within the barrel so that reciprocating movement of the plunger within the barrel is restricted;

inserting the needle into the tissue desired for analysis;

actuating a triggering means by applying a force to the triggering means whereby the triggering means moves in response to the force and the external restricting means disengages the internal restricting means such that the plunger is free to slidably reciprocate within the barrel;

withdrawing the plunger from its fully inserted position rapidly thereby creating a negative pressure within the barrel and drawing tissue into the needle; and releasing the application of force to the triggering means whereby the triggering means moves in response to the removal of the force and the external restricting means engages the internal restricting means such that the plunger is restricted from freely slidable reciprocation within the barrel and trapping tissue within the needle.

* * * * *

UNITED STATES PATENT AND TRADEMARK OFFICE
CERTIFICATE OF CORRECTION

PATENT NO. : 5,047,015

DATED : SEPTEMBER 10, 1991

INVENTOR(S) : JERROLD L. FOOTE ET AL.

It is certified that error appears in the above-identified patent and that said Letters Patent is hereby corrected as shown below:

```
Abstract, line 22, "angel" should be --angle--
Column 4, line 61, "preferrably" should be --preferably--
Column 6, line 30, "treadedly" should be --threadedly--
Column 8, line 32, "over compression" should be --overcompression--
Column 9, line 10, "5)" should be --50--
Column 9, line 16, delete ","
Column 10, line 19, "appications" should be --applications--
Column 12, line 51, after "means" insert --is--
Column 12, line 52, delete "is"
Column 13, line 65, ";" should be --,--
Column 16, line 44, ";" should be --,--
Column 13, line 9, ";" should be --,--
Column 13, line 22, ";" should be --,--
Column 13, line 52, ";" should be --,--
Column 14, line 7, ";" should be --,--
Column 14, line 10, "comprising" should be --comprises--
Column 15, line 8, ";" should be --,--
Column 15, line 31, "dispose on" should be --disposed on--
Column 15, line 41, "rom" should be --from--

Column 15, line 50, ";" should be --,--
Column 15, line 54, "ore" should be --one--
Column 15, line 63, ";" should be --,--
Column 16, line 14, ";" should be --,--
```

UNITED STATES PATENT AND TRADEMARK OFFICE
CERTIFICATE OF CORRECTION

PATENT NO. : 5,047,015
DATED : SEPTEMBER 10, 1991
INVENTOR(S) : JERROLD L. FOOTE ET AL.

It is certified that error appears in the above-identified patent and that said Letters Patent is hereby corrected as shown below:

```
Column 16, line 31, ";" should be --,--
Column 16, line 55, ";" should be --,--
Column 16, line 58, "comprising" should be --comprises--
Column 18, line 24, ";" should be --,--
Column 18, line 41, ";" should be --,--
Column 18, line 49, "to restrict" should be --restricting--
Column 19, line 42, "comprising" should be --which comprises--
Column 20, line 58, after "operating" insert --a--
Column 20, line 59, after "between" insert --a--
Column 20, line 62, "is" should be --being--
```

Signed and Sealed this

Thirty-first Day of August, 1993

*Attest:*

BRUCE LEHMAN

*Attesting Officer*   Commissioner of Patents and Trademarks

UNITED STATES PATENT AND TRADEMARK OFFICE
CERTIFICATE OF CORRECTION

| | | |
|---|---|---|
| PATENT NO. | : 5,047,015 | Page 1 of 1 |
| APPLICATION NO. | : 07/434460 | |
| DATED | : September 10, 1991 | |
| INVENTOR(S) | : Jerrold L. Foote et al. | |

It is certified that error appears in the above-identified patent and that said Letters Patent is hereby corrected as shown below:

Column 14, line 57
Change "restricted" to --unrestricted--.

Signed and Sealed this

Nineteenth Day of December, 2006

JON W. DUDAS
*Director of the United States Patent and Trademark Office*